(12) United States Patent
Zhang et al.

(10) Patent No.: US 9,518,973 B1
(45) Date of Patent: Dec. 13, 2016

(54) METHOD FOR DETERMINING THE AMOUNT OF OAT FLOUR ADDITION IN COMPOUND FLOURS AND NOODLES

(71) Applicants: Hui Zhang, Wuxi (CN); Chaoqun Wang, Wuxi (CN); Xiguang Qi, Wuxi (CN); Li Wang, Wuxi (CN); Haifeng Qian, Wuxi (CN)

(72) Inventors: Hui Zhang, Wuxi (CN); Chaoqun Wang, Wuxi (CN); Xiguang Qi, Wuxi (CN); Li Wang, Wuxi (CN); Haifeng Qian, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 0 days.

(21) Appl. No.: 14/975,554

(22) Filed: Dec. 18, 2015

(30) Foreign Application Priority Data

Oct. 13, 2015 (CN) .......................... 2015 1 0672104

(51) Int. Cl.
  *G01N 33/10* (2006.01)
  *G01N 33/02* (2006.01)
  *G01N 33/92* (2006.01)

(52) U.S. Cl.
  CPC .............. *G01N 33/10* (2013.01); *G01N 33/02* (2013.01); *G01N 33/92* (2013.01); *Y10T 436/25* (2015.01)

(58) Field of Classification Search
  CPC ........ G01N 33/02; G01N 33/92; Y10T 436/25
  USPC ....... 436/20, 71, 161, 174; 422/89; 210/656; 702/27, 32
  See application file for complete search history.

(56) References Cited

U.S. PATENT DOCUMENTS

| | | | |
|---|---|---|---|
| 2007/0292583 A1* | 12/2007 | Haynes | .................. A21D 13/02 426/549 |
| 2014/0099421 A1* | 4/2014 | Zhao | ...................... A21D 2/145 426/549 |

* cited by examiner

*Primary Examiner* — Maureen Wallenhorst
(74) *Attorney, Agent, or Firm* — Lili Chen

(57) ABSTRACT

The invention relates to a method for determining the amount of oat flour addition in compound flours and noodles, and it belongs to the field of food detection technology. Based on the similarity of the fatty acid composition between oat and wheat, the quantitative analysis index used for measuring the oat flour addition was determined. Based on the differences of fatty acid contents in oat and wheat, the relationship between the changing trend of fatty acid composition and oat flour content in compound powders or noodles is employed to quantitatively determine the amount of oat added to these compound flours or noodles. The invention provides a highly sensitive and feasible method for safety monitoring and quality control of oat flours and oat noodles.

8 Claims, 7 Drawing Sheets

METHOD FOR DETERMINING THE AMOUNT OF OAT FLOUR ADDITION IN COMPOUND FLOURS AND NOODLES

CROSS-REFERENCES AND RELATED APPLICATIONS

This application claims the benefit of priority to Chinese Application No. 201510672104.1, entitled "A method for determining the amount of oat flour addition in compound flours and noodles", filed Oct. 13, 2015, which is herein incorporated by reference in its entirety.

BACKGROUND OF THE INVENTION

1. Field of the Invention

The invention belongs to the field of food detection technology. In particular, it relates to a method for measuring the amount of oat flour addition in compound flours and noodles.

2. Description of the Related Art

Oat is the sixth most important cereal crop in the world, which is rich in variety and widely planted in China. Oat has high value in medical applications, health protection and cosmetic applications, for example, it can used in the prevention of vascular sclerosis and colon carcinoma, and improvement of immunity. Currently, there are many researches on oats at home and aboard, and there are a large varieties of oat products in the market. Oat flour plays an important role in breakfast cereals and flour products containing oat flour as an ingredient, where the most common ones are oat flours and noodles blended with oat. With addition of oats in the food, it brings more nutritious components to the food.

Although oat is widely used in flour products, there are also some major issues. Driven by economic interests, there is food adulteration on the market, especially adulteration of raw materials. For example, adding wheat flour to oat flour in order to reduce raw material costs, or adding a small amount of oats in oat products but charging more with less are common problems in food products. These food adulteration issues not only affect customer health and their economic interests, but also have a negative influence on the whole food industry chain. However, current research on detection of adulteration in flour products and monitoring of the flour production process is very rare. There is no accurate detection method for resolving this issue, thus making it impossible to establish a standard for quality control of cereal products. This is a large oversight in cereal food quality control management. Therefore, to establish a cereal food quality monitoring method is an imminent task. On one hand, this method will facilitate promotion and popularization of new and improved products, improve food quality, and enhance the overall level of cereal products; on the other hand, this method will provide a good database and a reference point for monitoring cereal adulteration in the food industry.

Ning Wang and his colleagues (2014) have researched the method for determining the amount of wheat flour adulterated in oat flour using a near infrared spectroscopy (NIR), balanced incomplete block design (BIBD) and least square analysis method. Although using NIR, an indirect analysis technology, to monitor cereal adulteration has advantages such as high speed, non-damage and non-pollution, there are many disadvantages as well. Firstly, a large amount of representative samples with known chemical data are needed to build a database and set up a quantitative model. Secondly, the conditions used to establish the model, such as particle size, moisture content, color, purity, test conditions, pretreatment method, can affect the accuracy of the detection. Furthermore, limited by the detection technology, different instruments with different models can result in instrumental errors. With continuous change of instrument models and changes in food samples, the quantitative model cannot be used universally, thus resulting in the increased cost of re-establishing models. Lastly, the accuracy of corresponding chemical values also needs to be validated.

DETAILED DESCRIPTION

Brief Summary of the Invention

The present invention provides a method for measuring the amount of oat flour addition in compound flours and noodles. The detection method is as follows:

Wheat flours and oat flours of different varieties and from different production areas are blended together to make a compound powder according to the balanced incomplete block design. The composition of fatty acids of the wheat flour, the oat flour and the compound powder with wheat flour and oat flour are determined by gas chromatography. Then the similarities and differences of contents of palm acid, oleic acid and linoleic acid are analyzed, and a 3D graph of discriminant analysis model and linear discriminant functions are established on the basis of the correlations in the contents of palm acid, oleic acid and linoleic acid, and the paired ratios of oleic acid, linoleic acid and palm acid in order to reveal the relationship between fatty acid distribution characteristics of the compound powder and oat flour addition in it, and the amount of oat flour addition is determined quantitatively according to the fatty acid distribution characteristics of the compound powder. The coefficient of variation of fatty acids in compound noodle as compared to the compound powder that makes up the compound noodle is further determined and calculated, which is used to adjust values of the contents or ratios of fatty acids. The adjusted values are then applied to the 3D graph of discriminant analysis and linear discriminant function so as to determine the amount of oat flour addition in the compound noodles.

The oat flour addition used herein refers to the amount of oat flour in the compound powders made by mixing wheat flour and oat flour, and the compound noodles made of such compound powders.

In a preferred embodiment, the present invention provides a method for measuring the amount of oat flour addition in compound flours and compound noodles, comprising the following steps:

(1) oat seeds and wheat seeds of different varieties and from different source areas are collected as many as possible, which are matched and paired into groups according to the balanced incomplete block design to obtain samples for establishing a quantitative model; and then the oat flour and the wheat flour in each group are blended together to make a compound flour with oat flour content between 0% to 30%;

(2) fatty acid information including contents of palm acid, oleic acid and linoleic acid of the oat flour, the wheat flour and the compound powder made of the oat flour and the wheat flour are determined by gas chromatography, and ratios of oleic acid and linoleic acid, palm acid and oleic acid, palm acid and linoleic acid are also calculated for each type of flour;

(3) 3D graph of discriminant analysis is established using contents of palm acid, oleic acid and linoleic acid, or the ratios of oleic acid and linoleic acid, palm acid and oleic acid, palm acid and linoleic acid as X, Y, and Z axis, respectively;

(4) The contents of palm acid, oleic acid, linoleic acid, or the ratios of oleic acid and linoleic acid, palm acid and oleic acid, palm acid and linoleic acid are used as independent variables to establish Fisher linear discriminant analysis and construct linear discriminant functions, which can be used to analyze the amount of oat flour added in the compound powder. The contribution rate of each variable to the model sample's discrimination ability is analyzed by Wilks' principle of $\lambda$ minimum statistics, final discriminant function is thus established based on its contribution to discrimination ability, and sample back tests are further carried out to verify the quantitative model.

(5) contents of palm acid, oleic acid and linoleic acid are determined in the unknown wheat-oat compound flour, and the value of contents or paired ratios of palm acid, oleic acid and linoleic acid are entered into the corresponding 3D graph of discriminant analysis model in step 3) and the corresponding linear discriminant functions in step 4) to calculate the amount of oat flour added in the unknown wheat-oat compound flour.

(6) Calculate coefficients of variation for fatty acids in compound noodle as compared to compound powder that is used to make the compound noodle, and use the coefficients of variation to adjust the corresponding values of contents or ratios of fatty acids in unknown wheat-oat compound noodle. Apply adjusted values of fatty acids to the 3D graph of discriminant analysis model in step 3) and the linear discriminant functions in step 4) to quantitatively determine the amount of oat added in the unknown wheat-oat compound noodle.

In a preferred embodiment, the present invention provides a method for determining the oat flour addition in compound flours, comprising the following steps:

a). Collecting oat and wheat of different varieties: oat and wheat seeds are collected from as many as possible different varieties and origins, including 30 to 50 oat varieties and 30 to 50 wheat varieties;

b). Dividing and pairing the collected oat and wheat varieties into groups according to the BIBD method to obtain samples for establishing quantitative models;

c). Pretreating raw materials and preparing compound powder with oat and wheat flour: oat seeds are purified, smashed and sieved to make oat flours; wheat seeds are processed in the way similar to industrial wheat flour processing cycle including removal of wheat bran, smashing and sieving; and the wheat flour and the oat flour in each group are mixed together to make compound flours with different levels of the oat flour;

d). Extracting oil composition from the oat flour, the wheat flour and the compound flour;

e). Treating the oil compositions above with methyl esterification to obtain pretreated samples for gas chromatography analysis;

f). Analyzing the pretreated samples by gas chromatography to obtain a fingerprint of fatty acids;

g). Analyzing fatty acids in the oat and the wheat flours: major fatty acids in oat and wheat flours are determined qualitatively by gas chromatography using retention time comparison to a mixed standards and are determined quantitatively using an internal standard; and similarities and differences in contents of palm acid, oleic acid and linoleic acid between oat and wheat flours are analyzed, and Pearson correlation analysis of palm acid, oleic acid and linoleic acid in oat and wheat flours is performed using the SPSS software;

h). Analyzing major fatty acids in compound powders: contents of palm acid, oleic acid and linoleic acid in compound powders are determined by gas chromatography, and the ratios of oleic acid and linoleic acid, palm acid and oleic acid, palm acid and linoleic acid are then calculated;

i). Establishing a 3D graph of discriminant analysis model: 3D graph of discriminant analysis is established using contents of palm acid, oleic acid and linoleic acid, or the ratios of oleic acid and linoleic acid, palm acid and oleic acid, palm acid and linoleic acid as X, Y, and Z axis, respectively;

j). Establishing Fisher linear discriminant analysis and verifying its accuracy: the contents of palm acid, oleic acid, and linoleic acid, or the ratios of oleic acid and linoleic acid, palm acid and oleic acid, palm acid and linoleic acid are used as independent variables in Fisher linear discriminant analysis, which is used to determine the amount of oat flour added in the compound powders. The contribution of each variable to the model sample's discrimination ability is analyzed by Wilks' principle of $\lambda$ minimum statistics, final discriminant function is established based on its contribution to discrimination ability, and sample back tests are further carried out to verify the quantitative model.

k). the amount of oat flour addition in unknown oat-wheat compound powder is quantitatively determined by comprehensive study of the 3D graph and Fisher linear discriminant analysis.

l). Determining the amount of oat flour in unknown oat-wheat compound noodle: the coefficient of variation for fatty acids of compound noodles in comparison to the compound powder that makes up the compound noodles is determined and calculated, and use the coefficients of variation to adjust the corresponding values of contents or ratios of fatty acids in unknown wheat-oat compound noodle; and apply adjusted values of fatty acids to the 3D graph of discriminant analysis model and linear discriminant functions to quantitatively determine the amount of oat added in unknown wheat-oat compound noodles.

In the preferred embodiment above, the number of oat and wheat varieties in step a) are 48 and 40, respectively.

In the preferred embodiment above, in step b), oat and wheat samples are matched and divided into 35 groups according to the balanced incomplete block design, each group with three different mixing ratios, each ratio repeated for 15 times, with a total of 105 model samples.

In the preferred embodiment above, in the step b), according to stratified random sampling, 35 oat samples are selected from 48 oat varieties that are from 10 origin areas, and 35 wheat samples are selected from 40 wheat varieties that are from 6 origin areas; the oat and wheat samples are matched and divided into 35 groups according to the balanced incomplete block design, and each group has 3 treatments. All treatments add up to 105 blended samples which satisfy basic BIBD condition, which is bk=rt, wherein the size of group k=3, the treatment number t=7, the number of group $b=C^3_7=35$, number of each treatment replication r=15, and replication number of matched pairs of any two treatments in the whole experiment $\lambda$=5.

In the preferred embodiment above, the compound powder in step c) has an oat flour content of 0%, 5%, 10%, 15%, 20%, 25%, 30% because redundant oat flour can affect the product's taste, extensibility, elasticity and stability.

In the preferred embodiment above, the oil composition in step d is extracted by Soxhlet extraction method.

In the preferred embodiment above, the methyl esterification method in step e) is as follows:

1). adding 20 mg oil sample into a 10 ml centrifuge tube;
2). adding 2 mL 0.5 mol/L NaOH—CH$_3$OH solution as a methyl esterification reagent into the 10 ml centrifuge tube, vortexing and reacting at 65□ for 30 min until oil beads are completely dissolved;
3). adding 2 mL 25% BF$_3$—CH$_3$OH into the 10 ml centrifuge tube after it is mixed, and letting it stand cool for 5 min; and then vortexing it and reacting at 65° C. for 20 min, and letting it stand cool again;
4). adding 2 ml hexane into the 10 ml centrifuge tube and vortexing it;
5). adding 2 ml saturated NaCl solution into the 10 ml centrifuge tube and vortexing it;
6). removing the upper organic phase into a drying vial after centrifugation at the speed of 3000 r/min for 15 min, and then adding 0.35 g anhydrous Na$_2$SO$_4$ to the organic phase to remove trace moisture. Final product is stored at −4° C. for gas chromatography.

In the preferred embodiment above, conditions for gas chromatography in step f) are as follows: PEG-20M capillary column (30 m×0.32 mm, 0.25 μm); gas: nitrogen; purge flow: 3 mL/min; injection volume: 1 μL; split ratio: 100:1; inlet temperature: 250° C.; temperature program: the initial temperature is 80° C., 3 min, increase the temperature to 215° C. at the speed of 15° C./min, keep the temperature for 16 min, and the solvent delay time is 1.5 min.

In the preferred embodiment above, the mixed standard solution in step f) is a mixture with 37 sigma standard fatty acid methyl esters, the internal standard is nonadecanoic acid, and the analysis of major fatty acids of oat and wheat includes content, amplitude, coefficient of variation and correlation relationships of the fatty acids. Compared with the existing technologies, the present invention provides a method for determining the amount of oat flour in compound powders and noodles that for the first time uses the balanced incomplete block design, gas photography measurement, and 3D graph and linear Fisher discriminant analysis. The present invention uses the balanced incomplete block design to select oat and wheat samples for building a quantitative model. The composition information of fatty acids in oat flours, wheat flours and compound powders are determined using gas chromatography, and similarity and difference of palm acid, oleic acid and linoleic acid in above flours are analyzed. 3D graph of discriminant analysis and linear discriminant function are established on the basis of the contents or paired ratios of oleic acid, linoleic acid, and palm acid in order to reveal relationship between fatty acid distribution characteristics and the amount of oat flour in the compound powders. The amount of oat flour in compound powders is quantitatively determined based the characteristics of fatty acid distribution. Furthermore, the coefficient of variation of fatty acids in compound noodles in comparison to compound powders that make up the compound noodles is calculated, and the 3D graph of discriminant analysis and linear discriminant function for determining the amount of oat flour in oat noodle is thus adjusted based on the coefficients.

The present invention is suitable for determining the oat content in compound flours and noodles made of different varieties of oats and wheat flours, which is the first precedent in the cereal product analysis and detection. The method of the present invention has a wide application range, is mature and stable, uses small amounts of samples, and offers the advantages of high separation efficiency, high detection sensitivity, and good selectivity.

DETAILED DESCRIPTION OF THE INVENTION 48 oat varieties from 10 origins and 40 wheat varieties from 6 origins were collected. Firstly, 35 oat samples and 35 wheat samples were selected based on stratified random sampling method, and then the selected oat and wheat samples were paired and matched using BIBD method. The oat seeds were treated with impurity removal, smashing and sieving to obtain oat flours, and the wheat seeds were treated with bran removal, smashing and sieving similar to industrial wheat flour processing procedure. The paired oat and wheat flours were mixed at different ratios to make compound powders according to the design of BIBD method. Secondly, oil composition of oat flours, wheat flours and compound powders with oat and wheat flour were extracted by Soxhlet method. The extracted oil composition was treated with methyl esterification and was then analyzed by gas chromatography. Fatty acids of samples were qualitatively identified by comparison to retention times of 37 mixed standard fatty acid methyl esters, and fatty acid contents were quantitatively analyzed using nonadecylic acid as the internal standard. The results showed that more than 90% of total fatty acids in oat flour and wheat flour are palm acid, oleic acid and linoleic acid, all of which have a small coefficient of variation. Correlation analysis of contents and paired ratios of palm acid, oleic acid and linoleic acid using 3D graph of discriminant analysis and Fisher linear discriminant function can visually present the distribution characteristics of fatty acids in the oat-wheat compound powder, which provides a theoretic basis for determining the content of oat in the compound powder based on its fatty acid distribution.

EXAMPLES

Figure 1:
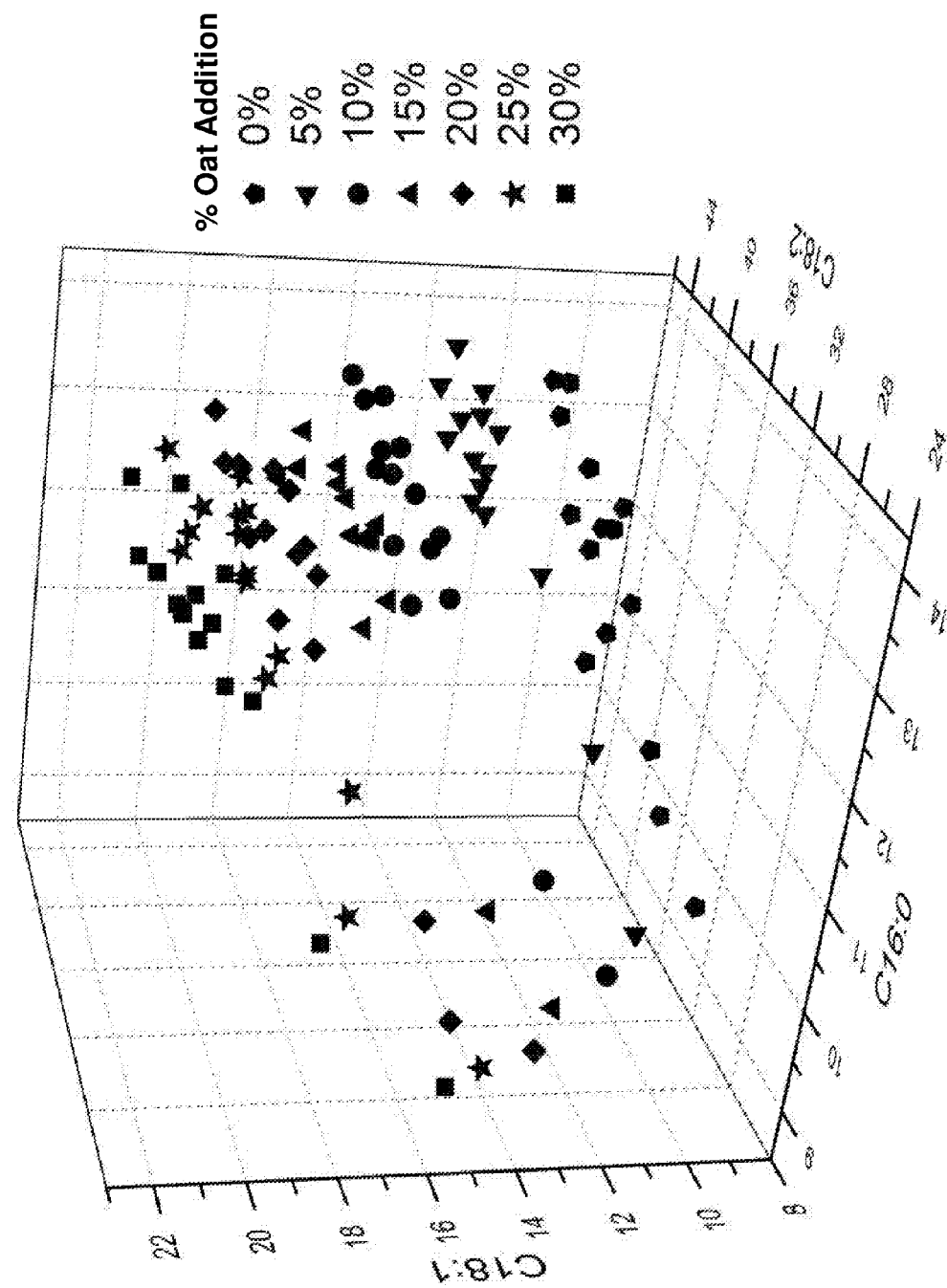
FIG. 1 is a 3D graph of discriminant analysis based on the contents of palm acid (C16:0), oleic acid (C18:1) and linoleic acid (C18:2) of 105 compound samples with different oat contents.

The following examples are provided for illustration purposes only, are not intended to limit the scope of the invention, which is limited only by the claims. The materials, agents, apparatus and methods used in following examples, if not specially stated otherwise, are commonly available materials, agents, apparatus and known methods in the art.

Example 1

Grouping and Pairing of Oat and Wheat Varieties According to BIBD

In order to make the quantitative model represent as much sample information as possible without expanding the sample size to impact test efficiency, the present invention uses the BIBD method to select samples within each group to have a good homogeneity, a good balance among groups and a good statistical coverage.

Firstly, 35 oat samples were selected from 48 different varieties that are from 10 origins, and 35 wheat samples were selected from 40 varieties that are from 6 origins using the stratified random sampling method. In order to balance the diversity of varieties and origins, oat and wheat samples were selected by a randomized process. 35 pairs of oat and wheat were randomly matched to form 35 groups and the group number of these 35 groups were randomized to balance the diversity. Seven different levels of oat addition were randomly distributed among the groups, and each group has three treatments. A total of 105 blended samples were thus obtained with 15 replicates of each oat addition level. This design satisfies basic BIBD requirement, that is, $bk=rt$, wherein the size of block (group) $k=3$, the number of treatments $t=7$, the number of blocks (groups) $b=C^3_7=35$, the number of each treatment replication $r=15$, and replication number of matched pairs of any two treatments in the whole experiment $\lambda=5$. Details are shown in Table 1.

TABLE 1

Selecting and Matching of oat and wheat samples

| Oat origin place | Oat variety | wheat origin | wheat variety | group | Random number of group | treatment1 | Treatment2 | Treatment 3 |
|---|---|---|---|---|---|---|---|---|
| Hebei | Bayou NO. 2 | Henan | Bainong207 | 1 | 34 | 0% | 5% | 10% |
| Gansu | Huazao NO.2 | Shanxi | Jinmai97 | 2 | 4 | 0% | 5% | 15% |
| Gansu | Bayou NO.12 | Shandong | Yannong5158 | 3 | 26 | 0% | 5% | 20% |
| Shanxi | Jinyan No.8 | Beijing | Nongda211 | 4 | 31 | 0% | 5% | 25% |
| Hebei | RDYZ-2 | Hebei | Le639 | 5 | 30 | 0% | 5% | 30% |
| Yunnan | Baiyan No.2 | Jiangsu | Huaimai18 | 6 | 20 | 0% | 10% | 15% |
| Jilin | BaiyanNo.2 | Beijing | Jingdong18 | 7 | 25 | 0% | 10% | 20% |
| Xinjiang | HuawanNo. 6 | Shanxi | Xinmai296 | 8 | 3 | 0% | 10% | 25% |
| Shanxi | BayanNo.1 | Shandong | Shandong22 | 9 | 13 | 0% | 10% | 30% |
| Shanxi | BayanNo.6 | Jiangsu | Huaimai30 | 10 | 16 | 0% | 15% | 20% |
| Neimeng | CaoyouNo. 1 | Henan | Yunong035 | 11 | 32 | 0% | 15% | 25% |
| Sichuan | Baiyan1No. 1 | Hebei | Cangmai6005 | 12 | 18 | 0% | 15% | 30% |
| Gansu | DingyouNo. 6 | Henan | Zhoumai26 | 13 | 1 | 0% | 20% | 25% |
| Yunnan | Zhaotong | Henan | Zhoumai 16 | 14 | 33 | 0% | 20% | 30% |
| Gansu | DingyouNo. 4 | Henan | Lankao198 | 15 | 11 | 0% | 25% | 30% |
| Gansu | DingyouNo. 7 | Jiangsu | Sukemai No.1 | 16 | 9 | 5% | 10% | 15% |
| Qinghai | Qingyin No.3 | Hebei | Jimai22 | 17 | 14 | 5% | 10% | 20% |
| Shanxi | Jinmai1 No.4 | Shanxi | Lunxuan167 | 18 | 2 | 5% | 10% | 25% |
| Qinghai | Qingyou No.3 | Hebei | Shixin828 | 19 | 7 | 5% | 10% | 30% |
| Shanxi | Yanke No.2 | Henan | Yunong416 | 20 | 10 | 5% | 15% | 20% |
| Gansu | 9628-3 | Shandong | Yannong21 | 21 | 24 | 5% | 15% | 25% |
| Xinjiang | BaiyanNo.2 | Henan | Zhengmai7698 | 22 | 22 | 5% | 15% | 30% |
| Gansu | 8652--3 | Jiangsu | Huaimai24 | 23 | 6 | 5% | 20% | 25% |
| Hebei | Jian44-625 | Shandong | Jimai No.2 | 24 | 35 | 5% | 20% | 30% |
| Ningxia | Yanke No.1 | Shanxi | Jinmai98 | 25 | 5 | 5% | 25% | 30% |
| Gansu | BaiyanNo.2 | Beijing | Jingdong22 | 26 | 8 | 10% | 15% | 20% |
| Gansu | Ningyou No.1 | Hebei | Shijiazhuang No.8 | 27 | 19 | 10% | 15% | 25% |
| Ningxia | BaiyanNo.2 | Shandong | Lumai21 | 28 | 15 | 10% | 15% | 30% |
| Shanxi | Yuanza No.2 | Shandong | Yannong19 | 29 | 27 | 10% | 20% | 25% |

TABLE 1-continued

Selecting and Matching of oat and wheat samples

| Oat origin place | Oat variety | wheat origin | wheat variety | Random group | number of group | treatment1 | Treatment2 | Treatment 3 |
|---|---|---|---|---|---|---|---|---|
| Qinghai | CaoyouNo.1 | Hebei | Jingdong22 | 30 | 21 | 10% | 20% | 30% |
| Shanxi | Bayou 1No.4 | Henan | Zhoumai24 | 31 | 28 | 10% | 25% | 30% |
| Hebei | Zhangyan No.7 | Shanxi | Changmai251 | 32 | 29 | 15% | 20% | 25% |
| Jilin | Baiyan No.8 | Shandong | Luyuan502 | 33 | 23 | 15% | 20% | 30% |
| Hebei | S20-171-9 | Beijing | Nongda3214 | 34 | 12 | 15% | 25% | 30% |
| Gansu | Dingyou No.8 | Henan | Zhoumai22 | 35 | 17 | 20% | 25% | 30% |

Example 2

Analysis of Fatty Acids in Oat Flour and Wheat Flour

Pretreatment of Samples

The impurities in oat seeds were removed, and the oat seeds were smashed by cyclone mill and 40-mesh sieved, thus obtaining oat flour. To prepare wheat flour, wheat seeds were smashed and 120-mesh sieved after bran removal similar to industrial wheat flour production process.

Extraction of Oil Composition from Flours

The oil composition of oat and wheat flours were extracted by Soxhlet method according to GB/T5512-2008.

Methyl Esterification of Fatty Acids 20 mg extracted oil sample was added into a 10 ml test tube, and 2 ml 0.5 mol/l freshly made NaOH—CH$_3$OH solution was added, and then the mixture was heated at 65° C. in a water bath until oil beads were completely dissolved (about 30 mins, samples were vortexed 2 to 3 times during the reaction). Let the mixture stand for cooling. 2 mL freshly formulated 25% BF$_3$—CH$_3$OH solution was added to the mixture and heated at 65° C. in a water bath for 20 minutes for a methyl esterification reaction. 2.0 mL hexane was added after the solution was cooled. After the reaction solution was vortexed adequately, 2 mL saturated NaCl solution was added. After centrifugation at 3000 r/min for 15 min, the upper organic phase was moved to a dry sample bottle, and small amount of anhydrous Na$_2$SO$_4$ was added into the bottle to remove trace moisture. The final product was stored at −4° C. for gas chromatography.

Gas Chromatography Analysis of Fatty Acid Composition

Fatty acids of flour samples were analyzed by gas chromatography under conditions as follows:

PEG-20M capillary column (30 m×0.32 mm, 0.25 μm); gas: nitrogen; purge flow: 3 mL/min; injection volume: 1 μL; split ratio: 100:1; inlet temperature: 250° C.; temperature program: the initial temperature is 80° C., 3 min, then increase the temperature to 215° C. at the speed of 15° C./min, keeping the temperature for 16 min, and the solvent delay time is 1.5 min.

Determination of Fatty Acid Contents

Fatty acids of flour samples were analyzed qualitatively by a mixture with 37 sigma standard fatty acid methyl esters, and were analyzed quantitatively using nonadecanoic acid as the internal standard.

Mass fraction of components determined by the internal standard method was calculated according to the following formula: $W_i = m_i/m \times 100\% = (f_i \times A_i \times m_s/f_s/A_s/m) \times 100\%$, wherein i is the component to be measured; $W_i$ is the mass fraction of the component i; $m_i$ is the mass of the component i; m is the mass of sample; $m_s$ is the mass of the internal standard component; $A_i$ and $A_s$ are peak areas of the component i and the internal standard component, respectively; $f_i$ and $f_s$ are quality correction factors of the component i and the internal standard component, respectively.

Analysis of Fatty Acid Composition in Oat and Wheat Flours

Table 2 and 3 show the composition, the average content, the amplitude of variation and the coefficient of variation of major fatty acids in pure oat and wheat flours. There are similarities and differences between those of oat and wheat flours. More than 90% of total fatty acids in both oat and wheat flours are three major fatty acids: palm acid, oleic acid and linoleic acid, all of which have small coefficients of variation. The coefficients of variation for palm acid, oleic acid and linoleic acid are 5.897%, 6.125%, 5.329% in oat and 4.529%, 7.862%, 1.570% in wheat, respectively. However, oat flour has an average of 39.169% of oleic acid which is significantly higher than that of wheat flour (15.531%). On the contrast, oat flour has an average of 37.735% of linoleic acid which is significantly lower than that of wheat flour (60.062%). Difference in palm acid contents between oat flour and wheat flour is small (15.863% in oat flour and 16.332% in wheat flour). Based on the similarities and differences of the fatty acid composition in oat and wheat flours, it provides a theoretical basis for quantitatively analysis of the oat content in the wheat-oat compound powder and noodle. Compared to other components with high variation coefficients, palm acid, oleic acid and linoleic acid are ideal representative indicators for establishing quantitative models that can be used widely.

TABLE 2

Fatty acid content in oat flour

| Fatty acid | Mean value % | Amplitude % | Coefficient of variation % |
|---|---|---|---|
| Myristic acid | 0.301 | 0.128~0.690 | 45.081 |
| Palm acid | 15.863 | 13.447~17.754 | 5.897 |
| Zoomaric acid | 0.196 | 0.062~0.423 | 33.760 |
| Trans zoomaric acid | 0.257 | 0.166~0.388 | 17.594 |
| Stearic acid | 2.309 | 1.875~2.985 | 11.241 |
| Oleic acid | 39.169 | 33.152~43.897 | 6.125 |
| Linoleic acid | 37.735 | 33.958~41.811 | 5.329 |
| Linolenic acid | 1.363 | 0.929~1.805 | 17.317 |
| Eicosanoic acid | 0.220 | 0.105~0.411 | 32.625 |
| Eicosenoic acid | 1.000 | 0.761~1.194 | 10.010 |
| Erucic acid | 0.673 | 0.066~2.187 | 84.566 |

TABLE 3

Fatty acid content in wheat flour

| Fatty acid | Mean value % | Amplitude % | Coefficient of variation % |
|---|---|---|---|
| Myristic acid | 0.134 | 0.089~0.199 | 21.805 |
| Pentadecane acid | 0.109 | 0.064~0.175 | 25.029 |
| Palm acid | 16.332 | 14.756~18.558 | 4.529 |
| Zoomaric acid | 0.259 | 0.152~0.418 | 24.248 |
| Trans zoomaric acid | 0.282 | 0.201~0.417 | 17.793 |
| Heptadecanoic acid | 0.130 | 0.074~0.251 | 31.811 |
| Stearic acid | 1.793 | 1.546~2.054 | 7.265 |
| Oleic acid | 15.531 | 12.189~18.764 | 7.862 |
| Linoleic acid | 60.062 | 58.181~62.398 | 1.570 |
| Linolenic acid | 3.501 | 2.868~4.510 | 13.037 |
| Eicosanoic acid | 0.183 | 0.102~0.298 | 26.706 |
| Eicosenoic acid | 0.798 | 0.498~1.021 | 15.156 |

Example 3

Determination of Fatty Acids Using Gas Chromatography

Precision Experiment

The same sample was pretreated as described in Example 2 and was repeated for 6 times of continuous injections in gas chromatography analysis. The results showed that the characteristic peaks of retention time RSD were less than 0.892%, peak areas RSD were less than 3.069%. These results showed a high accuracy of gas chromatography analysis.

Repeatability Experiment

Six solutions of the same sample were prepared and analyzed as described in Example 2. The results showed that the characteristic peaks of retention time RSD were less than 0.764%, peak area RSD were less than 4.249%. These results showed a good repeatability of gas chromatography analysis.

Stability Experiment

The same samples, which were treated as described in Example 2, were sealed and stored at −4° C. After 0 h, 4 h, 8 h, 12 h, 16 h, 20 h and 24 h, samples were analyzed using gas chromatography as described in Example 2. The results showed that the characteristic peaks of retention time RSD were less than 0.947%, peak area RSD were less than 4.556%, showing excellent stability.

TABLE 4

Results of precision, repeatability and stability of method

| | Relative standard deviation of retention time (%) | | | Relative standard deviation of peak area (%) | | |
|---|---|---|---|---|---|---|
| No. | Precision (n = 6) | Repeatability (n = 6) | stability (n = 6) | Precision (n = 6) | Repeatability (n = 6) | stability (n = 6) |
| 1 | 0.360 | 0.132 | 0.413 | 1.057 | 3.204 | 3.215 |
| 2 | 0.469 | 0.188 | 0.486 | 2.450 | 4.249 | 1.075 |
| 3 | 0.235 | 0.356 | 0.458 | 0.484 | 1.089 | 2.235 |
| 4 | 0.310 | 0.178 | 0.314 | 1.516 | 1.369 | 3.811 |
| 5 | 0.454 | 0.118 | 0.656 | 0.277 | 2.084 | 4.556 |
| 6 | 0.452 | 0.172 | 0.496 | 0.652 | 2.556 | 1.624 |
| 7 | 0.636 | 0.159 | 0.546 | 0.094 | 0.836 | 2.850 |
| 8 | 0.572 | 0.166 | 0.605 | 3.069 | 1.777 | 1.900 |
| 9 | 0.847 | 0.553 | 0.719 | 1.459 | 1.961 | 1.108 |
| 10 | 0.687 | 0.272 | 0.786 | 2.682 | 2.572 | 4.337 |
| 11 | 0.892 | 0.764 | 0.947 | 0.219 | 0.849 | 2.370 |

Example 4

Correlation Analysis of Fatty Acids in Oat, Wheat and Compound Powder and Establishment of 3D Graph of Discriminant Analysis Based on correction analysis of major fatty acids in oat and wheat flour (Table 5 and 6), the data show that there are negative correlations between palm acid and oleic acid, oleic acid and linoleic acid, oleic acid and Linolenic acid in oat and wheat flour. However, there is a positive correlation between linoleic acid and Linolenic acid.

TABLE 5

Correlation analysis of major fatty acids in oat flour

| Fatty acid in oat | Palm acid | Stearic acid | Oleic acid | Linoleic acid | Linolenic acid | Eicosenoic acid |
|---|---|---|---|---|---|---|
| Palm acid | 1 | | | | | |
| Stearic acid | 0.251 | 1 | | | | |
| Oleic acid | −.480** | −0.137 | 1 | | | |
| Linoleic acid | 0.059 | −0.078 | −.790** | 1 | | |
| Linolenic acid | 0.09 | −0.136 | −.424** | .538** | 1 | |
| Eicosenoic acid | −.344* | −0.182 | 0.27 | −0.18 | −0.081 | 1 |

TABLE 6

Correlation analysis of major fatty acids in wheat flour

| Fatty acid in wheat | Palm acid | Stearic acid | Oleic acid | Linoleic acid | Linolenic acid | Eicosenoic acid |
|---|---|---|---|---|---|---|
| Palm acid | 1 | | | | | |
| Stearic acid | 0.328 | 1 | | | | |
| Oleic acid | −.340* | 0.322 | 1 | | | |
| Linoleic acid | −0.134 | −.451** | −.643** | 1 | | |
| Linolenic acid | 0.122 | −.562** | −.854** | .563** | 1 | |
| Eicosenoic acid | 0.09 | 0.276 | .546** | −0.292 | −.588** | 1 |

Further correlation analysis of paired ratios of oleic acid/linoleic acid, palm acid/oleic acid and palm acid/linoleic acid in compound powders with different mixing levels was performed based on above-mentioned correlations. As shown in Table 7, there is significantly positive correlation between ratios of oleic acid/linoleic acid and palm acid/linoleic acid. However, the correlation of the ratios of oleic acid/linoleic acid and palm acid/oleic acid and the correlation of the ratios of palm acid/oleic acid and palm acid/linoleic acid are significantly negative.

TABLE 7

Correction analysis of the proportion of fatty acids

| Ratios | Oleic acid/linoleic acid | Palm acid/Oleic acid | Palm acid/linoleic acid |
|---|---|---|---|
| Oleic acid/linoleic acid | 1 | | |
| Palm acid/Oleic acid | −0.961** | 1 | |
| Palm acid/linoleic acid | 0.883** | −0.812** | 1 |

Based on above-mentioned correlations, 3D graph of discriminant analysis of oat flour addition was established. As shown in the 3D graph of discriminant analysis (FIGS. 1&2), the distribution of palm acid, oleic acid and linoleic acid in compound powders with different oat flour levels has shown certain distinguishable characteristics. There are significant differences in fatty acid distribution among compound powders with different oat levels.

Figure 2:
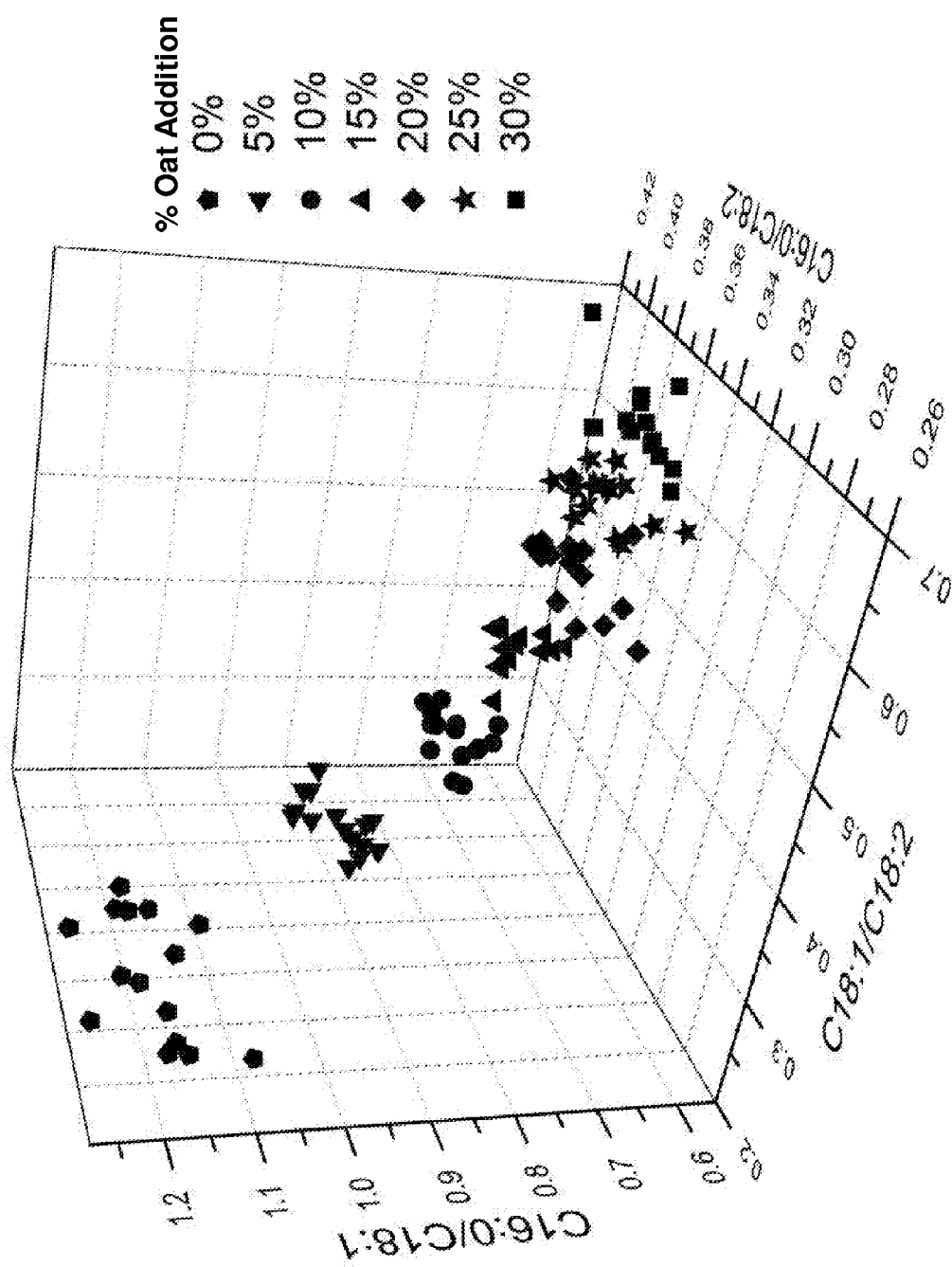
FIG. 2 is a 3D graph of discriminant analysis based on the ratios of oleic acid (C18:1) and linoleic acid (C18:2), palm acid (C16:0) and oleic acid (C18:1), palm acid (C16:0) and linoleic acid (C18:2) of 105 compound samples with different oat contents.

When the addition of oat flour is between 0% and 30%, oleic acid content in FIG. 1 and the ratio of palm acid/oleic acid in FIG. 2 have shown a significant decreasing trend and obvious regional effects, which can be used to quantify the amount of oat in the compound powder. For example, in FIG. 1, when the addition of oat flour is 5%, palm acid content is in the scale of 9.72~13.89%, oleic acid content is in the scale of 10.39~14.15%, and linoleic acid content is in the scale of 14.80~21.42%; when the addition of oat flour is 25%, palm acid content is in the scale of 9.27~13.46%, oleic acid content is in the scale of 14.80~21.42%, and linoleic acid content is in the scale of 25.47~37.00%; In FIG. 2, when the addition of oat flour is 5%, the ratio of oleic acid/linoleic acid is in the scale of 0.33~0.35, the ratio of palm acid/oleic acid is in the scale of 0.93~1.01, and the ratio of palm acid/linoleic acid is in the scale of 0.31~0.34; when the addition of oat flour is 25%, the ratio of oleic acid/linoleic acid is in the scale of 0.55~0.60, ratio of palm acid/oleic acid is in the scale of 0.34~0.38, and the ratio of palm acid/linoleic acid is in the scale of 0.58~0.67.

Example 5

Figure 3:
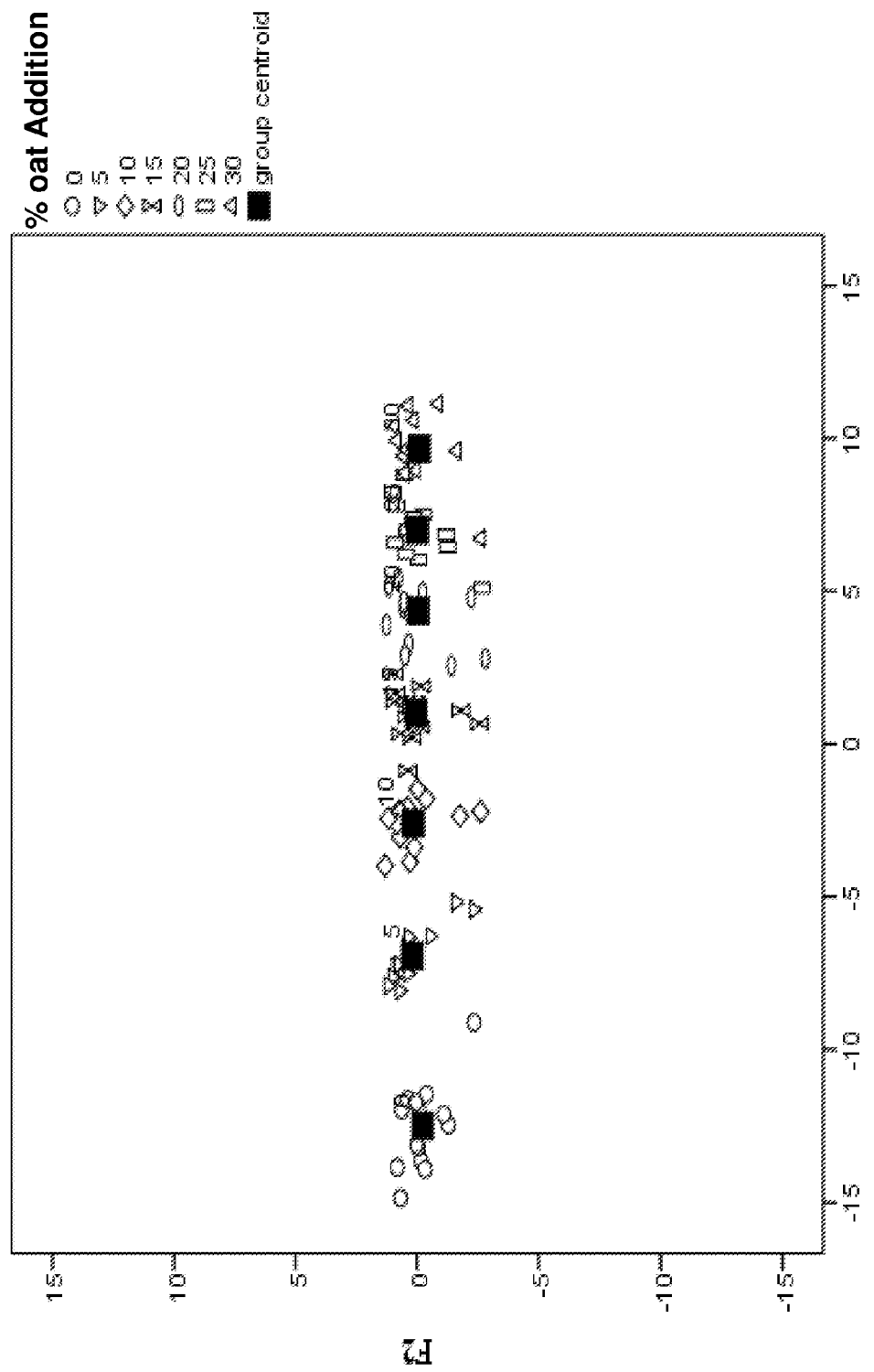
FIG. 3 is a graph of Fisher linear discriminant analysis based on the contents of palm acid, oleic acid, linoleic acid in 105 compound samples as independent variables. F1 and F2 refer to the discriminant function scores calculated from $F_1$ ($F_1 = -0.683X_1 + 1.641X_2 - 1.780$) and $F_2$ ($F_2 = 0.227X_1 + 0.169X_2 - 10.965$), respectively, wherein $X_1$ and $X_2$ refer to contents of linoleic acid and oleic acid of each sample, respectively.

Fisher Linear Discriminant Analysis and Verification of Accuracy (1) Fisher Linear Discriminant Analysis Using the Content of Three Fatty Acids as Independent Variables The amount of Oat flour addition of compound powder is analyzed by Fisher discriminant analysis using contents of palm acid, linoleic acid and oleic acid as independent variables $x_1$, $x_2$, $x_3$, respectively. The results shown that oleic acid and linoleic acid were into model, and two canonical discriminant functions were obtained as follows: $F_1=-0.683X_1+1.641X_2-1.780$, $F_2=0.227X_1+0.169X_2-10.965$ ($X_i$ is the content of i-th independent variable into model, wherein $X_1$ and $X_2$ refer to the contents of linoleic acid and oleic acid, respectively). Characteristic values of $F_1$ and $F_2$ are 57.135 and 0.019, and variance contribution rates of $F_1$ and $F_2$ are 100% and 0%, respectively. Therefore, the discriminant result of F1 is able to represent discriminant results obtained from these three indexes. The result of discriminant classification is better using Fisher linear discriminant function score (FIG. 3). The discriminant results were verified back to test. In 105 initial samples, 93.3% were classified accurately using mentioned method (shown in Table 8), and 92.4% samples in cross validation group were classified accurately. Thus, high accuracy of classification discrimination to oat flour addition ratio can be obtained using oleic acid and linoleic acid as indexes. Fisher linear discriminant functions of various ratios are as follows:

$$Y(0\%)=9.759X_1-15.777X_2-116.971$$

$$Y(5\%)=6.053X_1-6.568X_2-77.475$$

$$Y(10\%)=3.089X_1+0.525X_2-64.129$$

$$Y(15\%)=0.593X_1+6.433X_2-66.333$$

$$Y(20\%)=-1.712X_1+11.912X_2-80.348$$

$$Y(25\%)=-3.508X_1+16.249X_2-100.370$$

$$Y(30\%)=-5.346X_1+20.616X_2-126.609$$

wherein $X_1$, $X_2$ are the contents of the first and second independent variables into model, which refer to contents of linoleic acid and oleic acid, respectively.

TABLE 8

Results of Fisher linear discriminant analysis

| | | % of oat | 0 | 5 | 10 | 15 | 20 | 25 | 30 | total |
|---|---|---|---|---|---|---|---|---|---|---|
| self-verification | count | 0 | 14 | 1 | 0 | 0 | 0 | 0 | 0 | 15 |
| | | 5 | 0 | 15 | 0 | 0 | 0 | 0 | 0 | 15 |
| | | 10 | 0 | 0 | 15 | 0 | 0 | 0 | 0 | 15 |
| | | 15 | 0 | 0 | 1 | 14 | 0 | 0 | 0 | 15 |
| | | 20 | 0 | 0 | 0 | 1 | 13 | 1 | 0 | 15 |
| | | 25 | 0 | 0 | 0 | 0 | 1 | 13 | 1 | 15 |
| | | 30 | 0 | 0 | 0 | 0 | 0 | 1 | 14 | 15 |
| | % | 0 | 93.3 | 6.7 | 0 | 0 | 0 | 0 | 0 | 100 |
| | | 5 | 0 | 100 | 0 | 0 | 0 | 0 | 0 | 100 |
| | | 10 | 0 | 0 | 100 | 0 | 0 | 0 | 0 | 100 |
| | | 15 | 0 | 0 | 6.7 | 93.3 | 0 | 0 | 0 | 100 |
| | | 20 | 0 | 0 | 0 | 6.7 | 86.7 | 6.7 | 0 | 100 |

TABLE 8-continued

Results of Fisher linear discriminant analysis

|  |  | % of oat | Forecast group | | | | | | | total |
|---|---|---|---|---|---|---|---|---|---|---|
|  |  |  | 0 | 5 | 10 | 15 | 20 | 25 | 30 |  |
|  |  | 25 | 0 | 0 | 0 | 0 | 6.7 | 86.7 | 6.7 | 100 |
|  |  | 30 | 0 | 0 | 0 | 0 | 0 | 6.7 | 93.3 | 100 |
| cross-verification[a] | count | 0 | 14 | 1 | 0 | 0 | 0 | 0 | 0 | 15 |
|  |  | 5 | 0 | 15 | 0 | 0 | 0 | 0 | 0 | 15 |
|  |  | 10 | 0 | 0 | 15 | 0 | 0 | 0 | 0 | 15 |
|  |  | 15 | 0 | 0 | 1 | 14 | 0 | 0 | 0 | 15 |
|  |  | 20 | 0 | 0 | 0 | 2 | 12 | 1 | 0 | 15 |
|  |  | 25 | 0 | 0 | 0 | 0 | 1 | 13 | 1 | 15 |
|  |  | 30 | 0 | 0 | 0 | 0 | 0 | 1 | 14 | 15 |
|  | % | 0 | 93.3 | 6.7 | 0 | 0 | 0 | 0 | 0 | 100 |
|  |  | 5 | 0 | 100 | 0 | 0 | 0 | 0 | 0 | 100 |
|  |  | 10 | 0 | 0 | 100 | 0 | 0 | 0 | 0 | 100 |
|  |  | 15 | 0 | 0 | 6.7 | 93.3 | 0 | 0 | 0 | 100 |
|  |  | 20 | 0 | 0 | 0 | 13.3 | 80 | 6.7 | 0 | 100 |
|  |  | 25 | 0 | 0 | 0 | 0 | 6.7 | 86.7 | 6.7 | 100 |
|  |  | 30 | 0 | 0 | 0 | 0 | 0 | 6.7 | 93.3 | 100 |

[a]Only cross validation. In cross validation, each case is classified as a function of the others from the case.
[b]Correct classification of 93.3% of the initial packet has been carried out.
[c]Correct classification of 92.4% of the cross validation group cases has been carried out.

Figure 4:
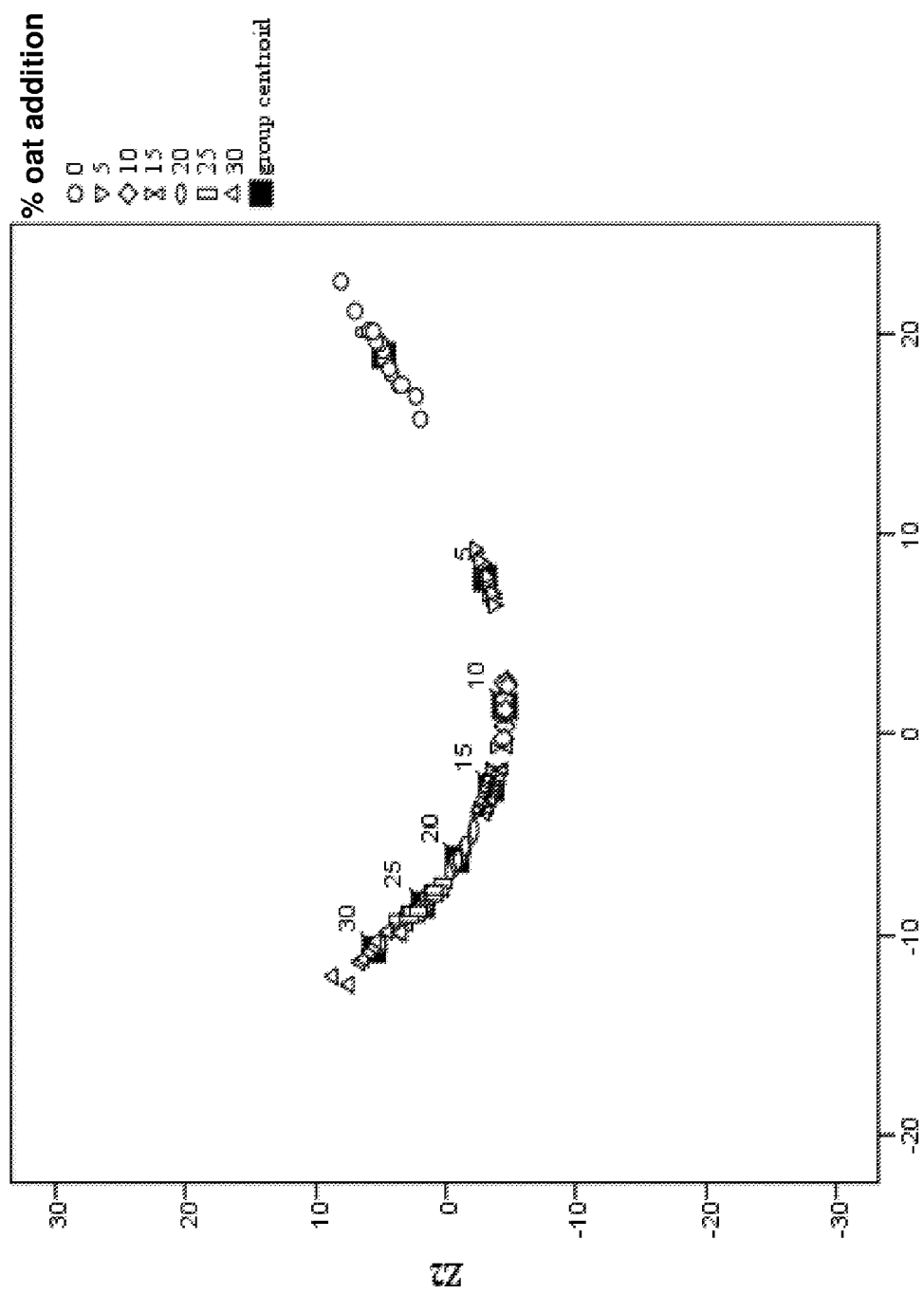
FIG. 4 is a graph of Fisher linear discriminant analysis based on the ratios of oleic acid and linoleic acid, palm acid and oleic acid, palm acid and linoleic acid of 105 blended samples as independent variables. Z1 and Z2 refer to the discriminant function scores calculated from function $Z_1$ ($Z_1 = 2.314Y_1 - 61.652Y_2 + 43.381Y_3 - 14.816$) and $Z_2$ ($Z_2 = 145.963Y_1 - 166.335Y_2 + 70.735Y_3 - 66.433$), respectively, wherein $Y_1$, $Y_2$ and $Y_3$ refer to ratios of oleic acid/linoleic acid, palm acid/linoleic acid, and palm acid/oleic acid, respectively.

(2) Fisher Linear Discriminant of Ratios of Three Fatty Acids as Independent Variables Oat flour addition of compound powder is analyzed by Fisher discriminant analysis using ratios of oleic acid/linoleic acid, palm acid/linoleic acid, and palm acid/oleic acid as independent variables $y_1$, $y_2$, $y_3$, respectively. The results shown that all three ratios were into the model, and three canonical discriminant functions were obtained as follows: $Z_1=2.314Y_1-61.652Y_2+43.381Y_3-14.816$; $Z_2=145.963Y_1-166.335Y_2+70.735Y_3-66.433$; $Z_3=-10.155Y_1+79.994Y_2+2.763Y_3-24.906$ ($Y_i$ is the content of i-th independent variable into model, wherein Y1, Y2 and Y3 refer to the ratios of oleic acid/linoleic acid, palm acid/linoleic acid, and palm acid/oleic acid, respectively.), Characteristic values of $Z_1$, $Z_2$ and $Z_3$ are 99.995, 15.021 and 0.031, and variance contribution rates of $Z_1$, $Z_2$ and $Z_3$ are 86.9%, 13.1% and 0.0% respectively. Therefore, the discriminant result of $Z_1$ and $Z_2$ are able to represent discriminant results used three indexes. The discriminant classification effect is better using discriminant function score of $Z_1$ and $Z_2$ (FIG. 4). The discriminant results were verified back to test. In 105 initial samples, 95.2% were classified accurately using mentioned method (shown in Table 8), and 93.3% samples in cross validation groups were classified accurately. Thus, high accuracy of classification discrimination to oat flour addition ratio can be obtained using ratios of oleic acid/linoleic acid, palm acid/linoleic acid, and palm acid/oleic acid as indexes. Fisher linear discriminant functions of various ratios are as follows:

$H(0\%)=10209.020Y_1-11929.600Y_2+6564.371Y_3-3408.860$;

$H(5\%)=9044.323Y_1-9913.550Y_2+5531.789Y_3-2582.910$;

$H(10\%)=8820.336Y_1-9314.010Y_2+5149.267Y_3-2354.890$;

$H(15\%)=8965.771Y_1-9225.640Y_2+5047.150Y_3-2367.790$;

$H(20\%)=9334.950Y_1-9456.310Y_2+5077.611Y_3-2491.510$;

$H(25\%)=9721.616Y_1-9747.400Y_2+5170.893Y_3-2660.880$;

$H(30\%)=10250.820Y_1-10212.200Y_2+5333.879Y_3-2908.670$ wherein Y1, Y2, Y3 are the ratios of the first, second and third independent variables into model, which refer to the ratios of oleic acid/linoleic acid, palm acid/linoleic acid, and palm acid/oleic acid, respectively.

TABLE 9

Results from Fisher linear discriminant analysis

| Verification[b,c] |  | % of oat | Forecast group | | | | | | | total |
|---|---|---|---|---|---|---|---|---|---|---|
|  |  |  | 0 | 5 | 10 | 15 | 20 | 25 | 30 |  |
| self-verification | count | 0 | 15 | 0 | 0 | 0 | 0 | 0 | 0 | 15 |
|  |  | 5 | 0 | 15 | 0 | 0 | 0 | 0 | 0 | 15 |
|  |  | 10 | 0 | 0 | 15 | 0 | 0 | 0 | 0 | 15 |
|  |  | 15 | 0 | 0 | 1 | 14 | 0 | 0 | 0 | 15 |
|  |  | 20 | 0 | 0 | 0 | 0 | 13 | 2 | 0 | 15 |
|  |  | 25 | 0 | 0 | 0 | 0 | 1 | 14 | 0 | 15 |
|  |  | 30 | 0 | 0 | 0 | 0 | 0 | 1 | 14 | 15 |
|  | % | 0 | 100 | 0 | 0 | 0 | 0 | 0 | 0 | 100 |
|  |  | 5 | 0 | 100 | 0 | 0 | 0 | 0 | 0 | 100 |
|  |  | 10 | 0 | 0 | 100 | 0 | 0 | 0 | 0 | 100 |
|  |  | 15 | 0 | 0 | 6.7 | 93.3 | 0 | 0 | 0 | 100 |
|  |  | 20 | 0 | 0 | 0 | 0 | 86.7 | 13.3 | 0 | 100 |
|  |  | 25 | 0 | 0 | 0 | 0 | 6.7 | 93.3 | 0 | 100 |
|  |  | 30 | 0 | 0 | 0 | 0 | 0 | 6.7 | 93.3 | 100 |
| cross-verification[a] | count | 0 | 15 | 0 | 0 | 0 | 0 | 0 | 0 | 15 |
|  |  | 5 | 0 | 15 | 0 | 0 | 0 | 0 | 0 | 15 |
|  |  | 10 | 0 | 0 | 15 | 0 | 0 | 0 | 0 | 15 |
|  |  | 15 | 0 | 0 | 1 | 14 | 0 | 0 | 0 | 15 |
|  |  | 20 | 0 | 0 | 0 | 0 | 13 | 2 | 0 | 15 |
|  |  | 25 | 0 | 0 | 0 | 0 | 1 | 13 | 1 | 15 |
|  |  | 30 | 0 | 0 | 0 | 0 | 0 | 2 | 13 | 15 |
|  | % | 0 | 100 | 0 | 0 | 0 | 0 | 0 | 0 | 100 |
|  |  | 5 | 0 | 100 | 0 | 0 | 0 | 0 | 0 | 100 |
|  |  | 10 | 0 | 0 | 100 | 0 | 0 | 0 | 0 | 100 |

TABLE 9-continued

Results from Fisher linear discriminant analysis

| Verifi-cation[b, c] | % of oat | Forecast group | | | | | | | |
|---|---|---|---|---|---|---|---|---|---|
| | | 0 | 5 | 10 | 15 | 20 | 25 | 30 | total |
| | 15 | 0 | 0 | 6.7 | 93.3 | 0 | 0 | 0 | 100 |
| | 20 | 0 | 0 | 0 | 0 | 86.7 | 13.3 | 0 | 100 |
| | 25 | 0 | 0 | 0 | 0 | 6.7 | 86.7 | 6.7 | 100 |
| | 30 | 0 | 0 | 0 | 0 | 0 | 13.3 | 86.7 | 100 |

[a]Only cross validation. In cross validation, each case is classified as a function of the others from the case.
[b]Correct classification of 95.2% of the initial packet has been carried out.
[c]Correct classification of 93.3% of the cross validation group cases has been carried out.

Example 6

Determination of the Amount of Oat Added in Compound Noodles

Figure 5:
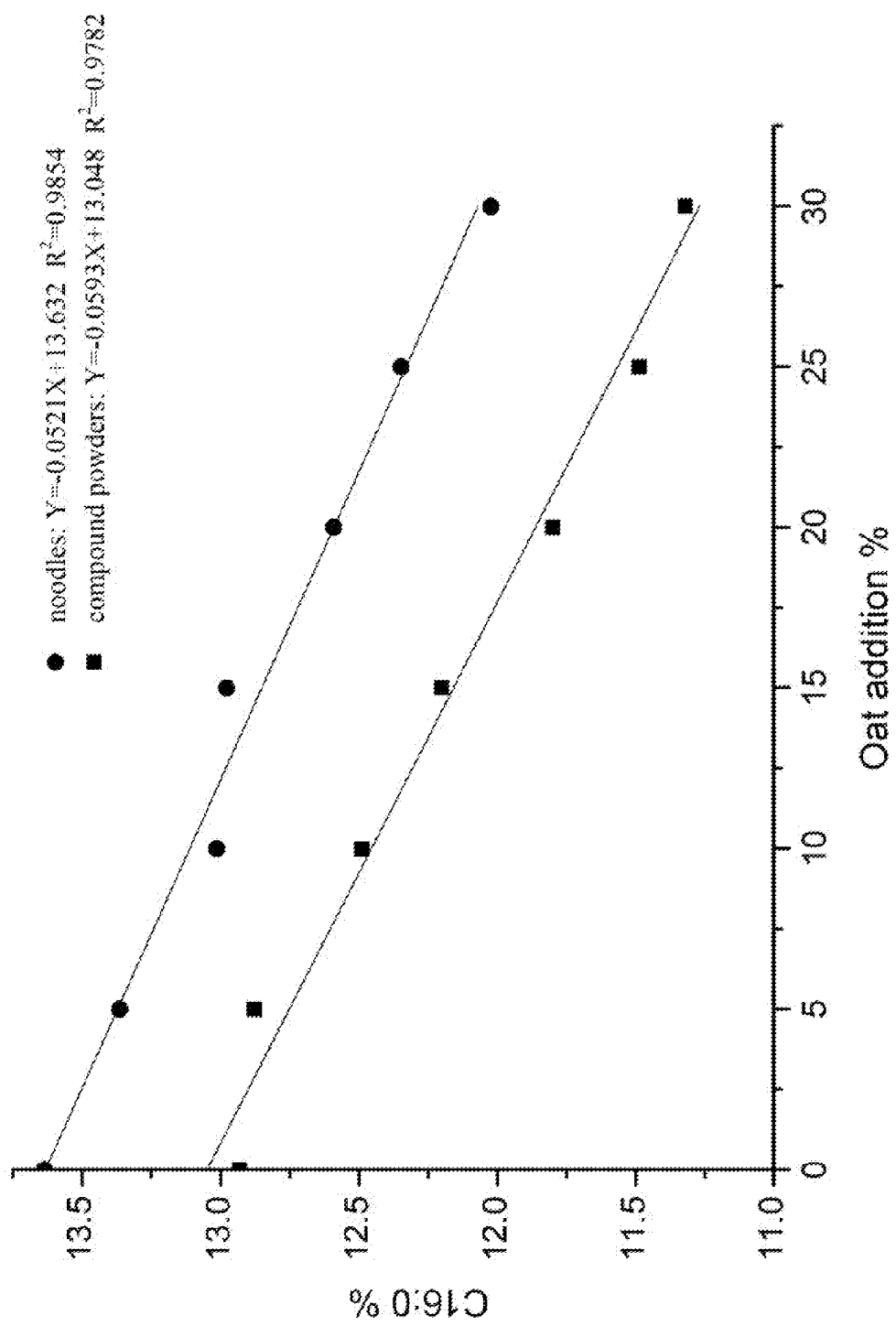
FIG. 5 is a comparison chart of palm acid contents in compound powders and noodles made of the compound powders.
Figure 6:
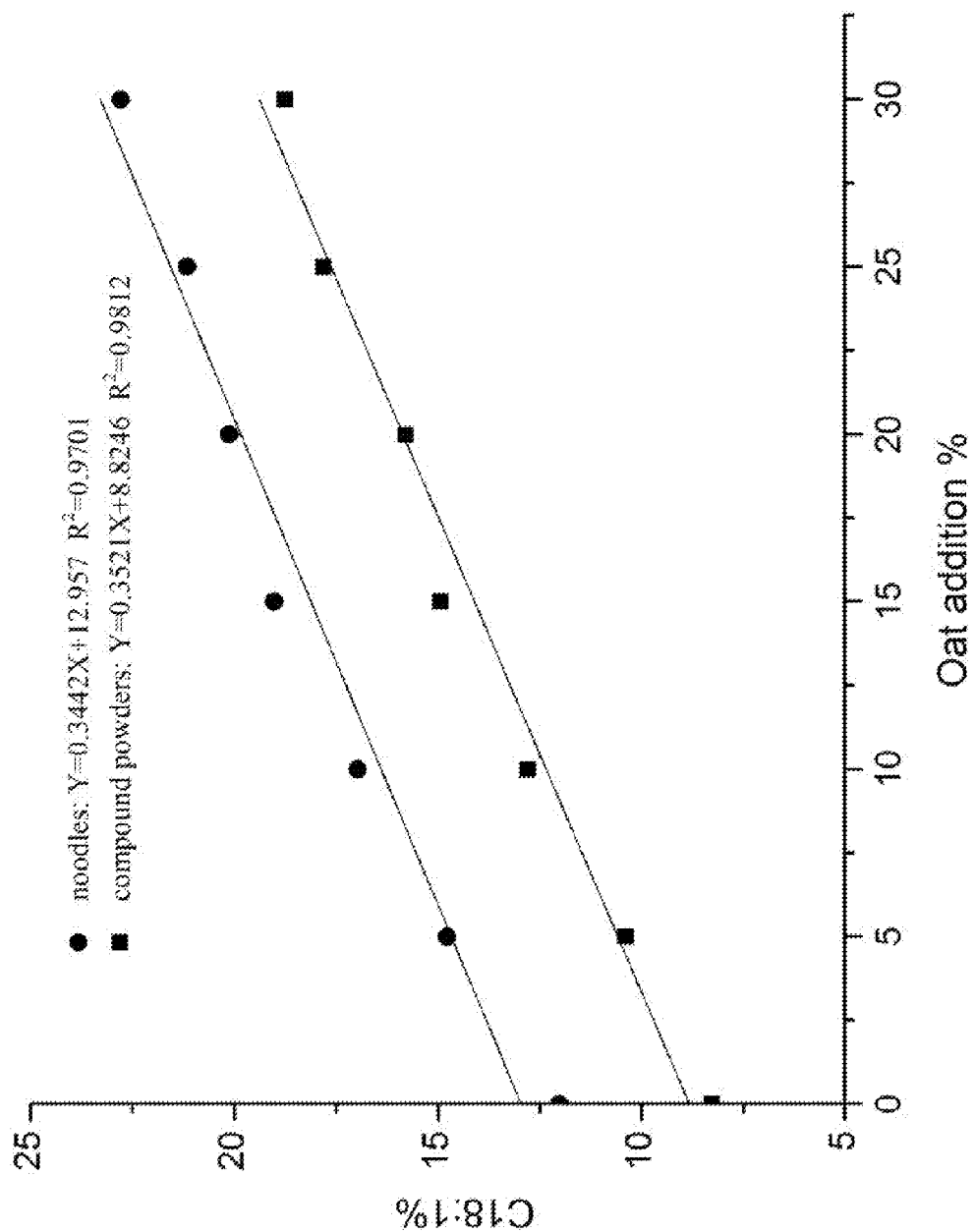
FIG. 6 is a comparison chart of oleic acid contents in compound powders and noodles made of the compound powders.
Figure 7:
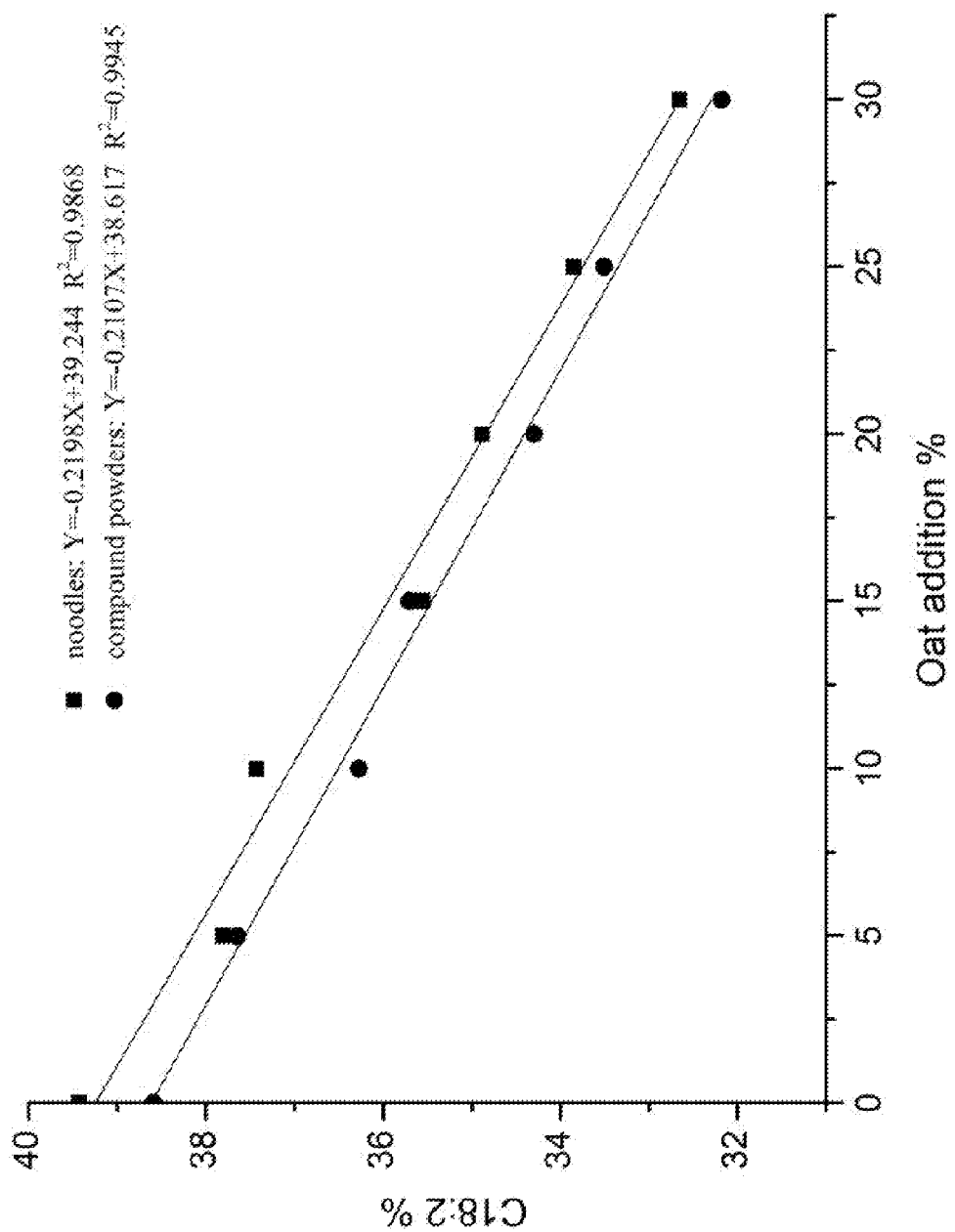
FIG. 7 is a comparison chart of linoleic acid contents in compound powders and noodles made of the compound powders.

Huazao No. 2 (oat from Gansu) and Jinmai 97 (wheat from Shanxi) were selected to be blended together with oat flour addition of 0%, 5%, 10%, 15%, 20%, 25% and 30% for producing compound powders that are used to make oat noodles. The contents of palm acid, oleic acid, and linoleic acid in compound powder and noodles were determined and analyzed. The results were shown in FIGS. 5, 6 and 7. The figures show that the contents of palm acid, oleic acid and linoleic acid in noodles are 1.04, 1.47 and 0.98 times as those in flour samples. Therefore, the ratios of oleic acid and linoleic acid, palm acid and oleic acid, palm acid and linoleic acid in noodles are 1.50, 0.71 and 1.06 times as those in flour samples. For noodles with unknown oat levels, the contents of three above-mentioned fatty acids in the oat noodles were determined, and adjusted by the coefficients of variation between oat powder and noodle (divided by the corresponding coefficients). The adjusted values can be used in the 3D graph and linear function of discriminant analysis to obtain the amount of oat addition in the oat noodle.

In order to determine the amount of oat flour addition in unknown compound powder or noodles, distribution characteristics of fatty acids in the unknown samples can be analyzed using 3D graph of discriminant analysis directly, and content scale of oat flour addition is obtained. Then, the contents and ratios (flour samples) or adjusted contents and ratios (noodle samples) of palm acid, oleic acid and linoleic acid of unknown samples can be entered into established Fisher linear discriminant function to calculate function scores, and levels of oat in the samples were determined based on the function scores. The highest Fisher linear discriminant function score determines the correct oat addition level. The method of this invention is suitable to apply to compound powder and noodles made of different varieties of oats and wheats that are widely circulated in the market.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method for determining the amount of oat flour addition in unknown compound wheat-oat flour or compound wheat-oat noodle, comprising the steps of:

a). Mixing oat and wheat flours of different varieties and from different production areas to make compound powders with different levels of oat flours according to a balanced incomplete block design;

b). Analyzing fatty acid compositions of the wheat flours, the oat flours and the compound powders by gas chromatography;

c). Analyzing similarities and differences of contents of palm acid, oleic acid and linoleic acid in the wheat flours, the oat flours and the compound powders;

d). Establishing a 3D graph of discriminant analysis model and Fisher linear discriminant functions based on correlations of contents or paired ratios of palm acid, oleic acid and linoleic acid and amounts of oat flour added in the compound powders;

e). Determining quantitatively the amount of oat flour addition in unknown compound wheat-oat flour using the 3D graph of discriminant analysis model and the Fisher linear discriminant functions established in step d);

f). Calculating coefficients of variation of fatty acids in a compound noodle as compared to the compound powder that is used to make the compound noodle, and using the coefficients of variation to adjust corresponding values of contents or ratios of fatty acids in unknown wheat-oat compound noodle; and g). Applying adjusted values of fatty acids to the 3D graph of discriminant analysis model and the Fisher linear discriminant functions to quantitatively determine the amount of oat added in unknown wheat-oat compound noodles.

2. The method of claim 1, wherein, in step a), oat and wheat flours are mixed to make compound powders containing 0%-30% oat flour;

wherein, in step d), the 3D graph of discriminant analysis model and the Fisher linear discriminant functions use contents of palm acid, oleic acid and linoleic acid, or ratios of oleic acid/linoleic acid, palm acid/oleic acid, and palm acid/linoleic acid as independent variables, Wilks' principle of $\lambda$ minimum statistics is used to analyze contribution of each independent variable to the discriminant analysis model and establish Fisher linear discriminant functions, and sample back tests are carried out to further verify the discriminant analysis model;

wherein, in step e), contents of palm acid, oleic acid and linoleic acid, or ratios of oleic acid/linoleic acid, palm acid/oleic acid, and palm acid/linoleic acid in unknown compound wheat-oat flour are applied in the 3D graph of discriminant analysis model and the Fisher linear discriminant functions established in step d) to calculate the amount of oat flour added in the unknown wheat-oat compound flour; and wherein, in step g), the contents of palm acid, oleic acid and linoleic acid, or the ratios of oleic acid/linoleic acid, palm acid/oleic acid, and palm acid/linoleic acid in the unknown compound wheat-oat flour are adjusted by the coefficients of variation of fatty acids, and adjusted contents or ratios of fatty acids are applied in the 3D graph of discriminant analysis model and the Fisher linear discriminant functions established in step d) to calculate the amount of oat flour added in the unknown compound wheat-oat noodle.

3. The method of claim 2, wherein 30 to 50 oat varieties and 30 to 50 wheat varieties are mixed in step a), and wherein the fatty acid composition of the wheat flours, the oat flours and the compound powders are pretreated with methyl esterification before the gas chromatography analysis in step b).

4. The method of claim 3, wherein 48 oat varieties and 40 wheat varieties are mixed in step a).

5. The method of claim 3, wherein the fatty acid compositions are extracted by Soxhlet extraction method in step d).

6. The method of claim 3, wherein the methyl esterification method in step b) comprises the following steps:
   1). adding 20 mg fatty acid sample into a 10 ml centrifuge tube;
   2). adding 2 mL 0.5 mol/L NaOH—$CH_3OH$ solution as a methyl esterification reagent into the 10 ml centrifuge tube, vortexing and reacting at 65° C. for 30 min until fatty acids are completely dissolved;
   3). adding 2 mL 25% $BF_3$—$CH_3OH$ into the 10 ml centrifuge tube after it is mixed, and letting it stand cool for 5 min; and then vortexing it and reacting at 65° C. for 20 min, and letting it stand cool again;
   4). adding 2 ml hexane into the 10 ml centrifuge tube and vortexing it;
   5). adding 2 ml saturated NaCl solution into the 10 ml centrifuge tube and vortexing it;
   6). removing upper organic phase into a dry vial, after centrifugation at a speed of 3000 r/min for 15 min, adding 0.35 g anhydrous $Na_2SO_4$ to the organic phase to remove trace moisture, and storing final products at 4° C. for gas chromatography.

7. The method of claim 3, wherein conditions of gas chromatography in step b) are as follows: PEG-20M capillary column; gas: nitrogen; purge flow: 3 mL/min; injection volume: 1 μL; split ratio: 100:1; inlet temperature: 250° C.; temperature program: initial temperature is 80° C., 3 min, increase the temperature to 215° C. at a speed of 15° C./min, keep the temperature at 215° C. for 16 min, and solvent delay time is 1.5 min.

8. The method of claim 2, wherein levels of the oat flours added to the compound powders in step a) are 0%, 5%, 10%, 15%, 20%, 25% and 30%.

* * * * *